(12) United States Patent
Ikeda et al.

(10) Patent No.: US 8,617,678 B2
(45) Date of Patent: Dec. 31, 2013

(54) CROSSLINKABLE COMPOSITION, CROSSLINKED PRODUCT AND METHOD FOR PRODUCTION THEREOF, MULTILAYERED STRUCTURE, CROSSLINKING AGENT, AND COMPOUND AND METHOD FOR PRODUCTION THEREOF

(75) Inventors: Kaoru Ikeda, Okayama (JP); Kazuhiro Kurosaki, Tokyo (JP)

(73) Assignee: Kuraray Co., Ltd., Kurashiki-shi (JP)

( * ) Notice: Subject to any disclaimer, the term of this patent is extended or adjusted under 35 U.S.C. 154(b) by 0 days.

(21) Appl. No.: 13/634,105

(22) PCT Filed: Mar. 10, 2011

(86) PCT No.: PCT/JP2011/055713
§ 371 (c)(1),
(2), (4) Date: Sep. 11, 2012

(87) PCT Pub. No.: WO2011/111802
PCT Pub. Date: Sep. 15, 2011

(65) Prior Publication Data
US 2013/0029070 A1 Jan. 31, 2013

(30) Foreign Application Priority Data

Mar. 11, 2010 (JP) .................................. 2010-055168
Mar. 11, 2010 (JP) .................................. 2010-055169

(51) Int. Cl.
*B29D 22/00* (2006.01)
*B29D 23/00* (2006.01)
*B32B 1/08* (2006.01)

(52) U.S. Cl.
USPC ............ 428/35.7; 525/59; 522/117; 564/153; 564/159; 428/474.4

(58) Field of Classification Search
USPC ................. 428/35.7, 474.4; 525/59; 522/117; 564/153, 159
See application file for complete search history.

(56) References Cited

U.S. PATENT DOCUMENTS

| 4,665,123 A | 5/1987 | Goldenberg |
| 5,283,196 A | 2/1994 | Hochstrasser et al. |

FOREIGN PATENT DOCUMENTS

| JP | 48 37246 | 11/1973 |
| JP | 49 26300 | 7/1974 |
| JP | 51 125018 | 11/1976 |
| JP | 62 32110 | 2/1987 |
| JP | 62 252409 | 11/1987 |
| JP | 2 503801 | 11/1990 |
| JP | 4 145055 | 5/1992 |
| JP | 5 271498 | 10/1993 |
| JP | 9 157421 | 6/1997 |
| JP | 9 234833 | 9/1997 |
| JP | 2004 277367 | 10/2004 |
| JP | 2006 49418 | 2/2008 |
| JP | 2011 2813 | 1/2011 |
| WO | 2007 123108 | 11/2007 |

OTHER PUBLICATIONS

International Search Report Issued Jun. 14, 2011 in PCT/JP11/55713 Filed Mar. 10, 2011.

*Primary Examiner* — Michael C Miggins
(74) *Attorney, Agent, or Firm* — Oblon, Spivak, McClelland, Maier & Neustadt, L.L.P.

(57) ABSTRACT

Providing a crosslinkable composition and a crosslinking agent is objected to, which are capable forming a crosslinked product that is superior in retort resistance, with suppressed bleeding out from the crosslinked product, and that has favorable interlayer adhesiveness when formed into a multilayered structure crosslinked product. The present invention provides a crosslinkable composition containing (A) a polymer having an SP value of no less than 9.5 $(cal/cm^3)^{1/2}$ and no greater than 16.5 $(cal/cm^3)^{1/2}$, and (B) a crosslinking agent having one or more polar groups that include an oxygen atom and a nitrogen atom not constituting an aromatic ring, and two or more polymerizable groups. The difference between the SP value of the polymer (A) and the SP value of the crosslinking agent (B) is preferably no greater than 2 $(cal/cm^3)^{1/2}$, and more preferably no greater than 1 $(cal/cm^3)^{1/2}$. A decomposition temperature of the crosslinking agent (B) is preferably no less than 240° C., and a melting point of the crosslinking agent (B) is preferably no greater than 220° C.

32 Claims, No Drawings

CROSSLINKABLE COMPOSITION, CROSSLINKED PRODUCT AND METHOD FOR PRODUCTION THEREOF, MULTILAYERED STRUCTURE, CROSSLINKING AGENT, AND COMPOUND AND METHOD FOR PRODUCTION THEREOF

TECHNICAL FIELD

The present invention relates to a crosslinkable composition, a crosslinked product obtained therefrom and a production method thereof, a multilayered structure in which a crosslinked product is used, a crosslinking agent, and a compound and a method for production thereof.

BACKGROUND ART

Polyvinyl alcohol type polymers, particularly ethylene-vinyl alcohol copolymers (hereinafter, merely referred to also as "EVOH") exhibit extremely small amount of oxygen transmission in comparison with other plastics, and favorable melt formability; therefore, they have been extensively used as food packaging materials and other packaging materials. However, when packaging materials produced using EVOH or the like are subjected to a retorting process under high-temperature and high-humid conditions, blooming and deformation may occur, or barrier properties may be deteriorated, and thus improvement of retort resistance has been demanded.

As a strategy for improving retort resistance and the like of packaging materials in which EVOH is used, various techniques in which EVOH is crosslinked using an activated energy ray such as an electron beam have been proposed. For example, Patent Document 1 discloses a method including melting and kneading triallyl cyanurate or triallyl isocyanurate used as a crosslinking agent, with EVOH, followed by irradiating with an electron beam to permit crosslinking of EVOH.

In addition, Patent Document 2 and Patent Document 3 disclose a procedure in which at least one crosslinking agent and/or crosslinking activator selected from a polyfunctional allylic compound, a polyfunctional (meth)acrylic compound, a polyhydric alcohol and a metal oxide is added to EVOH, and the mixture is irradiated with an electron beam to permit crosslinking.

Furthermore, Patent Document 4 describes that a compound having two or more allyl ether groups is added to EVOH, followed by irradiation with an electron beam to permit crosslinking.

Moreover, Patent Document 5 discloses a method in which an unmodified ethylene-vinyl alcohol type copolymer (A) is modified with an epoxy compound (B) having a double bond and an epoxy compound (E) not having a double bond, and at least a part of the obtained modified ethylene-vinyl alcohol type copolymer (C) is crosslinked with an electron beam.

However, according to the strategies of Patent Document 1 to Patent Document 4, the crosslinking agent remained in the resulting crosslinked product may bleed out. When such bleeding out occurs, hygienic problems are concerned particularly when a crosslinked product is used for food packing containers. In addition, when a multilayer film is produced by laminating a film obtained using the resulting crosslinked product, interlayer adhesiveness may be insufficient due to the bleeding out occurred, and yet the retort resistance can be further improved. Whereas, according to Patent Document 5, an especial extruder is needed for modifying EVOH, thereby leading to a problem of poor versatility.

PRIOR ART DOCUMENTS

Patent Documents

Patent Document 1: Japanese Unexamined Patent Application, Publication No. S62-252409
Patent Document 2: Japanese Unexamined Patent Application, Publication No. H5-271498
Patent Document 3: Japanese Unexamined Patent Application, Publication No. H9-157421
Patent Document 4: Japanese Unexamined Patent Application, Publication No. H9-234833
Patent Document 5: PCT International Publication No. 2007/123108

SUMMARY OF THE INVENTION

Problems to be Solved by the Invention

The present invention was made in view of the foregoing circumstances, and an object of the invention is to provide a crosslinkable composition and a crosslinking agent capable of providing a crosslinked product that is superior in retort resistance, with suppressed bleeding out from the crosslinked product, and that has favorable interlayer adhesiveness when formed into a multilayered structure.

Means for Solving the Problems

The present inventors studied the cause of the bleeding out as described above, and consequently found that inferior miscibility of the crosslinking agent with a material to be crosslinked would be involved. The present invention was accomplished on the basis of such a finding.

An aspect of the invention which was made for solving the foregoing problems provides a crosslinkable composition including (A) a polymer having an SP (i.e., Solubility Parameter) value of no less than 9.5 $(cal/cm^3)^{1/2}$ and no greater than 16.5 $(cal/cm^3)^{1/2}$ (hereinafter, also referred to as "polymer (A)"), and (B) a crosslinking agent having one or more polar groups that include an oxygen atom and a nitrogen atom not constituting an aromatic ring, and two or more polymerizable groups (hereinafter, also referred to as "crosslinking agent (B)").

In the crosslinkable composition, as a crosslinking agent for the polymer (A) having an SP value of no less than 9.5 $(cal/cm^3)^{1/2}$ and no greater than 16.5 $(cal/cm^3)^{1/2}$, (B) a crosslinking agent having one or more polar groups that include an oxygen atom and a nitrogen atom not constituting an aromatic ring, and two or more polymerizable groups is adopted. Since the crosslinking agent (B) has one or more specific polar group in the molecular structure, miscibility with the polymer (A) can be improved. As a consequence, the crosslinking agent can be prevented from remaining in the resulting crosslinked product, and in turn bleeding out of the crosslinking agent (B) can be prevented. In addition, due to an improvement of the miscibility of the crosslinking agent (B) with the polymer (A), even if the crosslinking agent remains in the crosslinked product after subjecting to a crosslinking treatment, whereby release from the crosslinked product can be suppressed, and thus prevention of occurrence of bleeding out is enabled. By thus suppressing the bleeding out, a crosslinked product can be provided which is hygienic and is superior in retort resistance, and which has favorable interlayer adhesiveness when formed into a multilayered structure. Furthermore, since the crosslinking agent (B) has two or more polymerizable groups, the crosslinkable composition containing the polymer (A) and the crosslinking agent (B) which are in a miscible state with each other may be merely irradiated with an activated energy ray or heated for producing the crosslinked product, whereby need of use of an especial instrument and the like for production can be obviated, and thus a crosslinked product can be efficiently produced.

According to the crosslinkable composition, the difference between an SP value of the polymer (A) and an SP value of the crosslinking agent (B) is preferably no greater than 2 (cal/cm$^3$)$^{1/2}$, and more preferably no greater than 1 (cal/cm$^3$)$^{1/2}$. When the difference between these SP values falls within the above range, a miscible state of the polymer (A) and the crosslinking agent (B) can be favorable, and easy and sufficient progress of a crosslinking reaction of the polymer (A) and the crosslinking agent (B) is enabled.

The crosslinking agent (B) has a decomposition temperature of preferably no less than 240° C. In a process for producing a crosslinked product, the crosslinking agent (B) may be brought into a miscible state with the polymer (A) when the polymer (A) is molded by melting and kneading at high temperatures. Also in such a case, when the crosslinking agent (B) has a decomposition temperature of no less than 240° C., decomposition of the crosslinking agent (B) during being melted and kneaded can be prevented, and a sufficient crosslinking level in the resulting crosslinked product can be attained.

The crosslinking agent (B) has a melting point of preferably no greater than 220° C. Accordingly, the miscible state of the crosslinking agent in the melting and kneading process as described above can be readily realized.

In the crosslinkable composition, it is preferred that the crosslinking agent (B) has an amide group as a polar group, and an unsaturated hydrocarbon group having 2 to 12 carbon atoms as a polymerizable group. When the crosslinking agent (B) has such a polar group and a polymerizable group, the miscibility with the polymer (A) can be improved, and sufficient progress of a crosslinking reaction of the polymer (A) and the crosslinking agent (B) by an activated energy ray, in particular, is facilitated.

The crosslinking agent (B) preferably includes 2 or 3 amide groups, and 2 or 3 unsaturated hydrocarbon groups having 2 to 12 carbon atoms. When the crosslinking agent (B) has such a structure, preparation or procurement of the crosslinking agent (B) can be easily executed while achieving an increase in miscibility with the polymer (A) and a degree of progression of the crosslinking reaction by an activated energy ray.

The polymerizable group of the crosslinking agent (B) is preferably a vinyl group, or an alkenyl group or an alkadienyl group having 3 to 12 carbon atoms. When the crosslinking agent (B) has such a specific group as the polymerizable group, smooth and sufficient progress of the crosslinking reaction with the polymer (A) by an activated energy ray is enabled.

The crosslinking agent (B) in the crosslinkable composition preferably has a structure represented by the following formula (1):

[chemical formula 1]

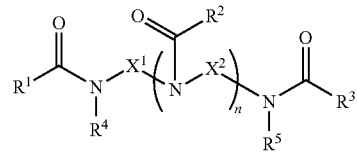

(1)

in the formula (1), $R^1$, $R^2$ and $R^3$ each independently represent an unsaturated hydrocarbon group having 2 to 8 carbon atoms; $R^4$ and $R^5$ each independently represent a hydrogen atom or an alkyl group having 1 to 4 carbon atoms; $X^1$ and $X^2$ each independently represent an alkanediyl group having 1 to 6 carbon atoms; and n is an integer of 0 to 4, and provided that n is an integer of at least 2, a plurality of $R^2$s each independently represent an unsaturated hydrocarbon group having 2 to 8 carbon atoms and a plurality of $X^2$s each independently represent an alkanediyl group having 1 to 6 carbon atoms.

When the crosslinking agent (B) has a specific structure represented by the above formula (1), miscibility with the polymer (A) is further improved, thereby permitting the crosslinking to sufficiently proceed. Thus, remaining of the crosslinking agent (B) in the crosslinked product can be further diminished, and moreover a crosslinked product that is hygienic and has favorable interlayer adhesiveness when formed into a multilayered structure can be provided.

According to the crosslinking agent (B), in the above formula (1), it is preferred that $R^1$, $R^2$ and $R^3$ each independently represent a vinyl group or an alkenyl group having 3 to 6 carbon atoms; $R^4$ and $R^5$ represent a hydrogen atom; $X^1$ and $X^2$ each independently represent an alkanediyl group having 1 to 3 carbon atoms; and n is 0 or 1. When the crosslinking agent (B) has such a specific structure, miscibility with the polymer (A) is further enhanced, thereby permitting the crosslinking of the polymer (A) with the crosslinking agent (B) to sufficiently proceed, and bleeding out of the crosslinking agent can be suppressed.

The polymer (A) is preferably a polyvinyl alcohol type polymer. By using a polyvinyl alcohol type polymer as the polymer (A), the resulting crosslinked product can exhibit superior gas barrier properties and the like.

The polyvinyl alcohol type polymer is preferably an ethylene-vinyl alcohol copolymer. When an ethylene-vinyl alcohol copolymer is used as the polyvinyl alcohol type polymer, melt formability of the crosslinkable composition, and gas barrier properties of the resulting crosslinked product can be satisfactory.

The crosslinkable composition is preferably for use in crosslinking by an activated energy ray. When the crosslinkable composition is for use in crosslinking by an activated energy ray, crosslinking can be performed by merely irradiating with an activated energy ray; therefore, a necessity of an especial extruder and the like is obviated, whereby a crosslinked product can be produced conveniently at low costs.

The activated energy ray for crosslinking of the composition is preferably an electron beam. When the activated energy ray for crosslinking of the composition is an electron beam, crosslinking of the polymer (A) with the crosslinking agent (B) can be smoothly and readily performed, thereby leading to suppression of bleeding, and thus a crosslinked product having favorable retort resistance and interlayer adhesiveness when formed into a multilayered structure can be provided.

According to another aspect, a crosslinked product provided by the present invention is obtained from the crosslinkable composition. The crosslinked product can exhibit suppressed likelihood of bleeding out, and favorable retort resistance and interlayer adhesiveness. The crosslinked product may be in the form of a film.

According to yet another aspect, a multilayered structure provided by the present invention has layers constituted with the crosslinked product. The multilayered structure can exert features of being accompanied by suppressed bleeding out of the crosslinking agent, and being superior in retort resistance and interlayer adhesiveness, and can concurrently achieve favorable hygienic properties. Therefore, the multilayered structure is suited for retort containers.

According to still another aspect, a method for producing a crosslinked product provided by the present invention includes a step of irradiating the crosslinkable composition with an activated energy ray. The crosslinkable composition enables a crosslinking reaction to smoothly and sufficiently proceed by irradiation with an activated energy ray. Among the activated energy rays, electron beams are suitable in light of crosslinking speed and crosslinking efficiency. Accordingly, a crosslinked product having suppressed likelihood of bleeding out, and favorable retort resistance and interlayer adhesiveness in combination can be efficiently produced.

According to other aspect, a crosslinking agent provided by the present invention is represented by the following formula (2):

[chemical formula 2]

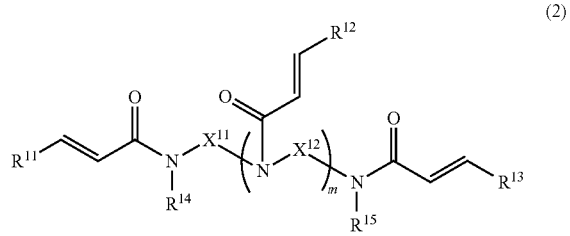

(2)

in the formula (2), $R^{11}$, $R^{12}$, $R^{13}$, $R^{14}$ and $R^{15}$ each independently represent a hydrogen atom or a hydrocarbon group which may have a substituent; $X^{11}$ and $X^{12}$ each independently represent a bivalent hydrocarbon group; m is an integer of 0 to 4, and provided that m is an integer of at least 2, a plurality of $R^{12}$s each independently represent a hydrogen atom or a hydrocarbon group which may have a substituent and a plurality of $X^{12}$s each independently represent a bivalent hydrocarbon group.

Since the crosslinking agent has a plurality of amide groups in the molecular structure, miscibility with a material to be crosslinked, for example, a polymer having an SP value of no less than 9.5 $(cal/cm^3)^{1/2}$ and no greater than 16.5 $(cal/cm^3)^{1/2}$, particularly a polyvinyl alcohol type polymer, etc., typified by EVOH can be improved. As a result, the crosslinking smoothly and sufficiently proceeds, whereby remaining of the crosslinking agent in the resulting crosslinked product can be prevented, and in turn, bleeding out of the crosslinking agent can be prevented. In addition, as a result of improved miscibility of the crosslinking agent with the material to be crosslinked, even if the crosslinking agent remains in the crosslinked product after the crosslinking treatment, release from the crosslinked product can be suppressed, whereby occurrence of bleeding out can be prevented. Moreover, since the crosslinking agent has a plurality of reactive groups, the material to be crosslinked and the crosslinking agent which are in a miscible state with each other may be merely irradiated with an activated energy ray for producing the crosslinked product, whereby need of use of an especial instrument and the like for production can be obviated, and thus a crosslinked product can be efficiently produced.

According to the crosslinking agent, in the above formula (2), it is preferred that $R^{11}$, $R^{12}$ and $R^{13}$ each independently represent a hydrogen atom or an alkyl group having 1 to 8 carbon atoms or an alkenyl group having 2 to 8 carbon atoms; $R^{14}$ and $R^{15}$ each independently represent a hydrogen atom or an alkyl group having 1 to 4 carbon atoms; $X^{11}$ and $X^{12}$ each independently represent an alkanediyl group having 1 to 6 carbon atoms; and m is an integer of 0 to 4. When the crosslinking agent has such a structure, miscibility with the material to be crosslinked is further improved, thereby permitting the crosslinking to sufficiently proceed. Thus, remaining of the crosslinking agent in the crosslinked product can be further diminished, and further a crosslinked product that is hygienic and has favorable interlayer adhesiveness can be provided.

According to the crosslinking agent, in the above formula (2), it is more preferred that $R^{11}$, $R^{12}$ and $R^{13}$ represent an alkyl group having 1 to 4 carbon atoms; $R^{14}$ and $R^{15}$ represent a hydrogen atom; $X^{11}$ and $X^{12}$ each independently represent an alkanediyl group having 1 to 3 carbon atoms; and m is 0 or 1. When the crosslinking agent has such a specific structure, miscibility with the material to be crosslinked is further enhanced, thereby permitting the crosslinking of the material to be crosslinked to sufficiently proceed by the crosslinking agent, and bleeding out of the crosslinking agent can be suppressed.

The crosslinking agent has a decomposition temperature of preferably no less than 240° C. In a process for producing a crosslinked product, when a material to be crosslinked such as EVOH is molded by melting and kneading at a high temperature, the crosslinking agent may be brought into a miscible state with EVOH, etc. Also in such a case, when the crosslinking agent has a decomposition temperature of no less than 240° C., decomposition of the crosslinking agent during melting and kneading can be prevented, and thus reaching to a sufficient crosslinking level in the resulting crosslinked product is enabled.

The crosslinking agent has a melting point of preferably no greater than 220° C. Accordingly, the miscible state of the crosslinking agent in the melting and kneading process as described above can be readily attained.

The crosslinking agent preferably has an SP value of no less than 11.0 $(cal/cm^3)^{1/2}$ and no greater than 14.5 $(cal/cm^3)^{1/2}$. When the SP value of the crosslinking agent falls within the above specific range, miscibility with a polymer having an SP value of no less than 9.5 $(cal/cm^3)^{1/2}$ and no greater than 16.5 $(cal/cm^3)^{1/2}$, particularly EVOH, can be enhanced, whereby, bleeding out from the crosslinked product can be prevented, and a crosslinked product that is superior in interlayer adhesiveness and retort resistance can be provided.

The crosslinking agent is preferably used for crosslinkage of a polyvinyl alcohol type polymer. By using the crosslinking agent for crosslinking of a polyvinyl alcohol type polymer, a crosslinked product having superior gas barrier properties and the like can be obtained.

The crosslinking agent is preferably for use in crosslinking of EVOH. When the crosslinking agent is for use in crosslinking of EVOH, melt formability of the resulting crosslinkable composition and favorable gas barrier properties of the crosslinked product obtained from this composition can be attained.

According to still other aspect, a compound provided by the present invention is represented by the following formula (2'):

[chemical formula 3]

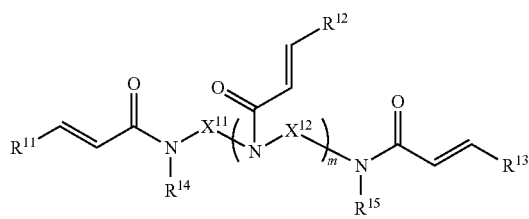

(2')

in the formula (2'), $R^{11}$, $R^{12}$ and $R^{13}$ each independently represent an alkyl group having 1 to 8 carbon atoms or an alkenyl group having 2 to 8 carbon atoms; $R^{14}$ and $R^{15}$ each independently represent a hydrogen atom or an alkyl group having 1 to 4 carbon atoms; $X^{11}$ and $X^{12}$ each independently represent an alkanediyl group having 1 to 6 carbon atoms; m is an integer of 0 to 4, and provided that m is an integer of at least 2, a plurality of $R^{12}$s each independently represent an alkyl group having 1 to 8 carbon atoms or an alkenyl group having 2 to 8 carbon atoms, and a plurality of $X^{12}$s each independently represent an alkanediyl group having 1 to 6 carbon atoms.

Since the compound has a specific structure represented by the above formula (2'), it can be suitably used as, for example, a crosslinking agent, etc., of the material to be crosslinked such as the polyvinyl alcohol type polymer.

According to yet other aspect, a method for producing a compound provided by the present invention has a step of allowing an unsaturated carboxylic acid derivative to react with a compound having at least two amino groups. According to the method for production, the compound can be efficiently produced.

As referred to herein, an expression of "an oxygen atom and a nitrogen atom not constituting an aromatic ring" means that any of the nitrogen atom and the oxygen atom does not constitute a cyclic skeleton of an aromatic ring. Furthermore, the "SP value" may be determined according to a formula of Fedors (Polym. Eng. Sci., 14[2], 147 (1974)).

Effects of the Invention

As explained in the foregoing, the crosslinkable composition and the crosslinking agent of the present invention are capable of providing a crosslinked product that is superior in retort resistance, with suppressed bleeding out from the crosslinked product, and that has favorable interlayer adhesiveness when formed into a multilayered structure.

DESCRIPTION OF EMBODIMENTS

Hereinafter, embodiments of the crosslinkable composition, crosslinked product and production method thereof, multilayered structure, crosslinking agent, and compound and production method thereof of the present invention will be explained in detail.

<Crosslinkable Composition>

The crosslinkable composition of the present invention includes (A) a polymer having an SP value of no less than 9.5 $(cal/cm^3)^{1/2}$ and no greater than 16.5 $(cal/cm^3)^{1/2}$, and (B) a crosslinking agent having one or more polar groups that include an oxygen atom and a nitrogen atom not constituting an aromatic ring, and two or more polymerizable groups, and as needed, other additive may be included. Since a specific crosslinking agent (B) is adopted as a crosslinking agent of (A) a polymer having an SP value of no less than 9.5 $(cal/cm^3)^{1/2}$ and no greater than 16.5 $(cal/cm^3)^{1/2}$ in the crosslinkable composition, miscible state of the two components becomes favorable, whereby stable and sufficient progress of crosslinking of the polymer (A) is enabled. As a result, bleeding out of the crosslinking agent (B) from the crosslinked product can be suppressed, and thus a crosslinked product that is superior in retort resistance and interlayer adhesiveness and that is hygienic can be provided. Hereinafter, each component is explained.

<(A) Component: Polymer Having an SP Value of No Less Than 9.5 $(cal/cm^3)^{1/2}$ and No Greater Than 16.5 $(cal/cm^3)^{1/2}$>

By using a polymer having an SP value of no less than 9.5 $(cal/cm^3)^{1/2}$ and no greater than 16.5 $(cal/cm^3)^{1/2}$ as the polymer (A), a crosslinked product can be obtained having improved retort resistance, interlayer adhesiveness and heat resistance, and additionally exhibiting suppressed bleeding out of the crosslinking agent. The SP value is preferably no less than 10.5 $(cal/cm^3)^{1/2}$ and no greater than 14.5 $(cal/cm^3)^{1/2}$, more preferably no less than 11.5 $(cal/cm^3)^{1/2}$ and no greater than 13.5 $(cal/cm^3)^{1/2}$, and particularly preferably no less than 12.0 $(cal/cm^3)^{1/2}$ and no greater than 13.0 $(cal/cm^3)^{1/2}$. When the SP value is less than 9.5 $(cal/cm^3)^{1/2}$ or greater than 16.5 $(cal/cm^3)^{1/2}$, bleeding out of the crosslinking agent occurs and a crosslinking rate decreases, whereby the retort resistance may be deteriorated.

The polymer (A) having an SP value of no less than 9.5 $(cal/cm^3)$ lie and no greater than 16.5 $(cal/cm^3)^{1/2}$ is not particularly limited as long as the SP value falls within this range, and is exemplified by (1) polyvinyl alcohol type polymer (10.6-14.1),
(2) cellulose (16.1),
(3) polyamide such as nylon-6 or nylon-66 (9.9-11.6),
(4) polyacrylonitrile (13.1),
(5) polyvinylidene chloride (10.4),
(6) polyethylene terephthalate (11.3), and the like.
It is to be noted that an SP value is shown in the parentheses, in terms of a unit of $(cal/cm^3)^{1/2}$.

Of these, in light of reactivity with the crosslinking agent (B), a polymer that includes a structural unit having a hydroxyl group is preferred, and further, in light of superior retort resistance and interlayer adhesiveness, and inhibition of bleeding out of the crosslinking agent, a polyvinyl alcohol type polymer described later is preferred, and an ethylene-vinyl alcohol copolymer is particularly preferred.

(Polyvinyl Alcohol Type Polymer)

A polyvinyl alcohol type polymers is obtained by saponification of a homopolymer of a vinyl ester, or a copolymer of a vinyl ester and other monomer (particularly, a copolymer of vinyl ester and ethylene) using an alkali catalyst or the like. Although a typical compound as the vinyl ester is exemplified by vinyl acetate, other fatty acid vinyl ester (vinyl propionate, vinyl pivalate, etc.) may be also used.

The degree of saponification of the vinyl ester component of the aforementioned polyvinyl alcohol type polymer is preferably no less than 90 mol %, more preferably no less than 95 mol %, and still more preferably no less than 96 mol %. When the degree of saponification is less than 90 mol %, oxygen barrier properties under highly humid conditions may be deteriorated. In addition, when the polyvinyl alcohol type polymer is an ethylene-vinyl alcohol copolymer (saponification product of a copolymer of ethylene and a vinyl ester; hereinafter, merely referred to also as "EVOH"), thermal stability may be insufficiently provided when the degree of saponification is less than 90 mol %, and the resultant molded product is likely to be accompanied by generation of gel or degraded material.

When the polyvinyl alcohol type polymer is constituted with a mixture of two or more types of polyvinyl alcohol type polymers having each distinct degree of saponification, an average value calculated on the basis of a mass ratio of mixing is defined as a degree of saponification of the mixture.

Of the polyvinyl alcohol type polymers as described above, EVOH is preferable in possibility of melt molding, and favorable oxygen barrier properties of the resultant crosslinked product under highly humid conditions.

The ethylene content of EVOH is preferably 5 to 60 mol %. When the ethylene content is less than 5 mol %, oxygen barrier properties of the crosslinked product under highly humid conditions are impaired, and melt formability may be also deteriorated. The ethylene content of EVOH is preferably no less than 10 mol %, more preferably no less than 15 mol %, and most preferably no less than 20 mol %. To the contrary, the ethylene content exceeding 60 mol % may lead to failure in attaining sufficient oxygen barrier properties. The ethylene content is preferably no greater than 55 mol %, and more preferably no greater than 50 mol %.

EVOH that is preferably used has, as described above, an ethylene content of 5 to 60 mol %, and a degree of saponification of no less than 90 mol %. In a multilayered structure described later obtained by molding the crosslinked product that results from the crosslinkable composition, when superior impact peal resistance is desired, EVOH having an ethylene content of no less than 25 mol % and no greater than 55 mol %, and a degree of saponification of no less than 90 mol % and less than 99.9 mol % is preferably used.

When EVOH is constituted with a mixture of two or more types of EVOHs having each distinct ethylene content, an average value calculated on the basis of a mass ratio of mixing is defined as an ethylene content of the mixture. In this case, the difference between ethylene contents of EVOHs having the greatest ethylene content and the smallest ethylene content is no greater than 30 mol %, and the difference between the degrees of saponification is preferably no greater than 10 mol %. When these requirements are not satisfied, transparency of the crosslinkable composition may be impaired. The difference between the ethylene contents is more preferably no greater than 20 mol %, and more preferably no greater than 15 mol %. Also, the difference between the degrees of saponification is more preferably no greater than 7 mol %, and still more preferably no greater than 5 mol %. In a multilayered structure obtained by molding the crosslinked product that results from the crosslinkable composition, when balance of impact peal resistance and oxygen barrier properties at a higher level is desired, EVOH (b'1) having an ethylene content of no less than 25 mol % and no greater than 55 mol %, and a degree of saponification of no less than 90 mol % and less than 99 mol %, and EVOH (b'2) having an ethylene content of no less than 25 mol % and no greater than 55 mol %, and a degree of saponification of no less than 99 mol % are preferably used by mixing so as to give a blend mass ratio (b'1)/(b'2) of 5/95 to 95/5.

The ethylene content of EVOH and the degree of saponification may be determined by a nuclear magnetic resonance (NMR) method.

The EVOH may also include as a copolymerization unit a monomer unit other than the ethylene unit and the vinyl alcohol unit in a small amount within a range not to compromise an object of the present invention. Examples of the monomer include the following compounds, and the like, i.e.: α-olefins such as propylene, 1-butene, isobutene, 4-methyl-1-pentene, 1-hexene and 1-octene; unsaturated carboxylic acids such as itaconic acid, methacrylic acid, acrylic acid and maleic acid, salts thereof, partial or complete esters thereof, nitriles thereof, amides thereof, and anhydrides of the same; vinylsilane type compounds such as vinyltrimethoxysilane, vinyltriethoxysilane, vinyltri(β-methoxyethoxy)silane and γ-methacryloxypropyltrimethoxysilane; unsaturated sulfonic acids or salts thereof; unsaturated thiols; vinylpyrrolidones; and the like.

Among the aforementioned other monomers, in the case in which EVOH contains a vinylsilane compound as a copolymerization component in an amount of no less than 0.0002 mol % and no greater than 0.2 mol %, when a multilayered structure is obtained by subjecting the crosslinkable composition of the present invention containing EVOH to coextrusion molding or coinjection molding together with a polymer to be a base material (for example, polyester; hereinafter, "polyester" being merely referred to also as "PES"), consistency of the melt viscosity with the base material polymer is improved, whereby production of a homogenous molded product is enabled. As the vinylsilane type compound, vinyltrimethoxysilane, vinyltriethoxysilane or the like is preferably used.

Moreover, in order to impart flexibility to EVOH, it is also preferable to modify EVOH by a conventionally well-known method. In this case, even if oxygen barrier properties are somewhat deteriorated due to the modification for imparting flexibility, the oxygen transmission rate can be also regulated by adjusting the structure and amount of the crosslinking agent (B), and a production method of EVOH.

The SP value of EVOH is not particularly limited as long as the effects of the invention can be achieved, which is preferably 11.5 to 13.5 $(cal/cm^3)^{1/2}$, and more preferably 12.0 to 13.0 $(cal/cm^3)^{1/2}$. When the SP value of EVOH falls within the above range, favorable miscibility with the crosslinking agent can be attained, and a crosslinking reaction of both compounds is enabled to smoothly and sufficiently proceed, whereby bleeding out of the crosslinking agent can be suppressed.

Suitable melt flow rate (MFR) of EVOH (at 210° C., under load of 2,160 g, in accordance with JIS K7210) is 0.1 to 100 g/10 min, more preferably 0.5 to 50 g/10 min, and still more preferably 1 to 30 g/10 min.

<(B) Component: Crosslinking Agent>

The crosslinking agent (B) of the crosslinkable composition has one or more polar groups that include an oxygen atom and a nitrogen atom not constituting an aromatic ring, and two or more polymerizable groups.

The polar group is not particularly limited as long as an oxygen atom and a nitrogen atom not constituting an aromatic ring are included, and is exemplified by an amide group, a urethane group, a cyanate group, an isocyanate group, a urea group, and the like. Among these polar groups, an amide group is preferred. When the polar group is an amide group, miscibility of the crosslinking agent (B) and the polymer (A) becomes favorable, and a crosslinking reaction of both compounds is enabled to smoothly and sufficiently proceed, whereby bleeding out of the crosslinking agent can be suppressed.

The polymerizable group is not particularly limited as long as a crosslinking reaction with the polymer (A) can be caused, and for example, when the polymer (A) is a polyvinyl alcohol type polymer, an unsaturated hydrocarbon group, a carboxyl group, an epoxy group, an isocyanate group, and the like may be exemplified. Of these, an unsaturated hydrocarbon group is preferred in light of a possibility of readily permitting crosslinking with an activated energy ray. It is to be noted that a group that is a polar group and a polymerizable group, such as an isocyanate group, etc., it is counted in duplicate as respective functional groups (a polar group and a polymerizable group).

The unsaturated hydrocarbon group is not particularly limited as long as it is a group having at least one of an ethylenic unsaturated bond and an acetylenic unsaturated bond, and for example, an alkenyl group, an alkadienyl group, an alkatrienyl group, an arylalkenyl group, an alkynyl group, an alkadiynyl group, an alkatriynyl group, and the like may be exemplified. The unsaturated hydrocarbon group has carbon atoms of typically 2 to 12, more preferably 2 to 10, still more preferably 2 to 8, and particularly 3 to 8.

Examples of the alkenyl group include linear alkenyl groups such as a vinyl group, a propenyl group (allyl group), a butenyl group, a pentenyl group, a hexenyl group, a heptenyl group, an octenyl group, a nonenyl group and a decenyl group, branched chain alkenyl groups such as a 2-propenyl group, a 1-methylpropenyl group and a 2-methylpropenyl group, cyclic alkenyl groups such as a cyclobutenyl group, a cyclopentenyl group and a cyclohexenyl group, and the like.

Examples of the alkadienyl group include linear alkadienyl groups such as a butadienyl group, a pentadienyl group, a hexadienyl group, a heptadienyl group and an octadienyl group, branched chain alkadienyl groups such as a 1-methylpentadienyl group and a 2-methylpentadienyl group, and the like.

Examples of the alkatrienyl group include linear alkatriynyl groups such as a hexatrienyl group, a heptatrienyl group and an octatrienyl group, branched chain alkatrienyl groups such as a 1-methylhexatrienyl group and a 2-methylhexatrienyl group, and the like.

The arylalkenyl group is exemplified by a phenylvinyl group, a phenylpropenyl group, and the like.

Examples of the alkynyl group include linear alkynyl groups such as an ethynyl group, a propynyl group, a butynyl group, a pentynyl group, a hexynyl group, a heptynyl group and an octynyl group, branched chain alkynyl groups such as a 1-methylpropynyl group and a 2-methylbutynyl group, and the like.

Examples of the alkadiynyl group include linear alkadiynyl groups such as a butadiynyl group, a pentadiynyl group, a hexadiynyl group, a heptadiynyl group and an octadiynyl group, branched chain alkadiynyl groups such as a 1-methylpentadiynyl group and a 2-methylhexadiynyl group, and the like.

Examples of the alkatriynyl group include linear alkatriynyl groups such as a hexatriynyl group, a heptatriynyl group and an octatriynyl group, branched chain alkatriynyl groups such as a 1-methylheptatriynyl group and a 2-methyloctatriynyl group, and the like.

A part or all of hydrogen atoms of the unsaturated hydrocarbon group may be substituted by a substituent which may include a hetero atom. The hetero atom in this case is not particularly limited as long as it is an atom other than a carbon atom and a hydrogen atom, and for example, a halogen atom, an oxygen atom, a sulfur atom, a nitrogen atom, and the like may be exemplified. The halogen atom is exemplified by a fluorine atom, a chlorine atom, an iodine atom, a bromine atom, and the like. Specific examples of the substituent that includes a hetero atom include an alkoxy group, a halogen atom, a hydroxyl group, an oxygen atom ($=$O), a cyano group, and the like. The alkoxy group is preferably an alkoxy group having 1 to 5 carbon atoms, more preferably a methoxy group, an ethoxy group, an n-propoxy group, an i-propoxy group, an n-butoxy group and a t-butoxy group, and still more preferably a methoxy group and an ethoxy group.

The polymerizable group is preferably a vinyl group, or an alkenyl group or an alkadienyl group having 3 to 12 carbon atoms, more preferably a vinyl group, or an alkenyl group or an alkadienyl group having 3 to 8 carbon atoms, still more preferably a vinyl group or an alkenyl group having 3 to 6 carbon atoms, and particularly preferably a vinyl group or an alkenyl group having 3 to 5 carbon atoms. When the polymerizable group of the crosslinking agent (B) is such a specific group, smooth and sufficient progress of a crosslinking reaction with the polymer (A) is enabled.

In the crosslinking agent (B), there is no particular limitation as long as the number of the polar group is at least one, and the number of the polymerizable group is at least two, and these groups may be present in the same or different numbers. The type and the number of the polar group and the polymerizable group may be determined taking into consideration the miscibility with the polymer (A), the degree of crosslinking in the resultant crosslinked product, and the like. Accordingly, although the type and the number of the polar group and the polymerizable group are not limited, the crosslinking agent (B) includes preferably 2 or 3 amide groups and 2 or 3 unsaturated hydrocarbon groups having 2 to 12 carbon atoms, more preferably 2 amide groups and 2 unsaturated hydrocarbon groups having 2 to 12 carbon atoms, or 3 amide groups and 3 unsaturated hydrocarbon groups having 2 to 12 carbon atoms, and particularly preferably 2 amide groups and 2 unsaturated hydrocarbon groups having 2 to 8 carbon atoms, or 3 amide groups and 3 unsaturated hydrocarbon groups having 2 to 8 carbon atoms. When the crosslinking agent (B) has such a structure, preparation or procurement of the crosslinking agent (B) can be readily conducted while the miscibility with the polymer (A) and degree of progression of the crosslinking reaction are improved.

Specific structure of the crosslinking agent (B) may be exemplified by triallyl isocyanurate, a structure represented by the above formula (1), a structure represented by the above formula (2) and the like, and of these, a structure represented by the above formula (1) or formula (2) is preferred. When the crosslinking agent (B) has a specific structure represented by the above formula (1), miscibility with the polymer (A) is further improved, thereby permitting the crosslinking to sufficiently proceed. Thus, remaining of the crosslinking agent (B) in the crosslinked product can be further diminished, and further a hygienic crosslinked product that is excellent in interlayer adhesiveness when formed into a multilayered structure can be provided.

(Crosslinking Agent Represented by the Above Formula (1))

In the above formula (1), with regard to the unsaturated hydrocarbon group having 2 to 8 carbon atoms represented by $R^1$, $R^2$ and $R^3$, details in connection with the unsaturated hydrocarbon group described above may be adopted. Examples of the alkyl group having 1 to 4 carbon atoms represented by $R^4$ and $R^5$ include a methyl group, an ethyl group, an n-propyl group, an i-propyl group, an n-butyl group, a t-butyl group, and the like. Examples of the alkanediyl group having 1 to 6 carbon atoms represented by $X^1$ and $X^2$ include a methanediyl group, an ethanediyl group, an n-propanediyl group, an i-propane diyl group, an n-butanediyl group, an n-pentanediyl group, an n-hexanediyl group, and the like. With regard to the unsaturated hydrocarbon group having 2 to 8 carbon atoms and the alkanediyl having 1 to 6 carbon atoms when $R^2$ and $X^2$ are present in a plurality of number, details of $R^2$ and $X^2$ described above may be adopted.

According to the crosslinking agent (B), it is preferred that in the above formula (1), $R^2$ and $R^3$ each independently represent a vinyl group or an alkenyl group having 3 to 6 carbon atoms; $R^4$ and $R^5$ represent a hydrogen atom; $X^1$ and $X^2$ each independently represent an alkanediyl group having 1 to 3 carbon atoms; and n is 0 or 1. When the crosslinking agent (B) has such a specific structure, miscibility with the polymer (A) is further enhanced, thereby enabling crosslinking of the polymer (A) with the crosslinking agent (B) to sufficiently proceed, and thus bleeding out of the crosslinking agent can be suppressed. In this case, with regard to the alkenyl group having 3 to 6 carbon atoms represented by $R^1$, $R^2$ and $R^3$, and the alkanediyl group having 1 to 3 carbon atoms represented by $X^1$ and $X^2$, details in connection with the alkenyl group and alkanediyl group may be adopted.

(Crosslinking Agent Represented by the Above Formula (2))

Also, the crosslinking agent preferably has a specific structure represented by the above formula (2). When the crosslinking agent has a structure represented by the above formula (2), particularly superior crosslinking reactivity with the polymer (A), and favorable miscibility can be provided. Accordingly, suppression of bleeding out of the crosslinking agent from the crosslinked product is enabled, and superior retort resistance and interlayer adhesiveness can be achieved.

In the above formula (2), the hydrocarbon group which may have a substituent represented by $R^{11}$, $R^{12}$, $R^{13}$, $R^{14}$ and $R^{15}$ is exemplified by an aliphatic hydrocarbon group, an alicyclic hydrocarbon group or an aromatic hydrocarbon group, and when these have a substituent, a part of carbon constituting the skeleton may be substituted with a substituent, or a part or all of hydrogen atoms may be substituted by a substituent.

The aliphatic hydrocarbon group may be a saturated aliphatic hydrocarbon group, or an unsaturated aliphatic hydrocarbon group. Also, the aliphatic hydrocarbon group may be either a linear or branched chain. In particular, the aliphatic hydrocarbon group is preferably a linear or branched chain saturated hydrocarbon group, or a linear or branched chain unsaturated hydrocarbon group.

The linear saturated hydrocarbon group (alkyl group) has carbon atoms of preferably 1 to 30, more preferably 1 to 20, still more preferably 1 to 8, and particularly preferably 1 to 4. Specific examples of the linear alkyl group include a methyl group, an ethyl group, a propyl group, a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, and the like.

The branched chain saturated hydrocarbon group (alkyl group) has carbon atoms of preferably 3 to 20, more preferably 3 to 15, and particularly preferably 3 to 10. Specific examples of the branched chain alkyl group include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, a 4-methylpentyl group, an isotridecyl group, an isohexadecyl group, and the like.

The unsaturated hydrocarbon group has carbon atoms of typically 2 to 12, preferably 2 to 10, more preferably 2 to 8, and still more preferably 2 to 4. Examples of the linear unsaturated hydrocarbon group include alkenyl groups such as a vinyl group, a propenyl group (allyl group), a butenyl group, pentenyl and hexenyl group, alkynyl groups such as an ethynyl group, a propynyl group, a butynyl group, a pentynyl group and a hexynyl group, and the like. Examples of the branched chain unsaturated hydrocarbon group include a 1-methylpropenyl group, a 2-methylpropenyl group, and the like.

Moreover, in the aliphatic hydrocarbon group, a part of carbon atoms constituting the aliphatic hydrocarbon group skeleton may be substituted with a substituent that includes a hetero atom, or a part or all of hydrogen atoms constituting the aliphatic hydrocarbon group may be substituted by a substituent that includes a hetero atom. The hetero atom in this case is not particularly limited as long as it is an atom other than a carbon atom and a hydrogen atom, and for example, a halogen atom, an oxygen atom, a sulfur atom, a nitrogen atom, and the like may be exemplified. The halogen atom is exemplified by a fluorine atom, a chlorine atom, an iodine atom, a bromine atom, and the like.

The substituent that includes a hetero atom may be only the hetero atom, or a group that includes a group or an atom other than the hetero atom.

Specific examples of the substituent that substitutes for a part of carbon atoms include —O—, —C(=O)—O—, —C(=O)—, —O—C(=O)—O—, —C(=O)—NH—, —NH— (wherein, H may be substituted by a substituent such as an alkyl group or an acyl group), —S—, —S(=O)$_2$—, —S(=O)$_2$—O—, and the like. On the other hand, specific examples of the substituent that substitutes for a part or all of hydrogen atoms as described above include an alkoxy group, a halogen atom, a hydroxyl group, an oxygen atom (=O), a cyano group, and the like.

The alkoxy group is preferably an alkoxy group having 1 to 5 carbon atoms, more preferably a methoxy group, an ethoxy group, an n-propoxy group, an i-propoxy group, an n-butoxy group, and a t-butoxy group, and still more preferably a methoxy group and an ethoxy group.

The halogen atom is exemplified by a fluorine atom, a chlorine atom, a bromine atom, an iodine atom and the like, and a fluorine atom is preferred.

The halogenated alkyl group is exemplified by an alkyl group having 1 to 5 carbon atoms, and examples include groups obtained by substituting by a halogen atom a part or all of hydrogen atoms of an alkyl group such as a methyl group, an ethyl group, a propyl group, an n-butyl group or a t-butyl group.

The alicyclic hydrocarbon group may be either a monocyclic group, or a polycyclic group. The alicyclic hydrocarbon group has carbon atoms of typically 3 to 30, preferably 5 to 30, more preferably 5 to 20, still more preferably 6 to 15, and particularly preferably 6 to 12. Specific examples of such an alicyclic hydrocarbon group include monocycloalkyl groups; polycycloalkyl groups such as bicycloalkyl, tricycloalkyl and tetracycloalkyl groups, and the like.

Further specific examples of the alicyclic hydrocarbon group include monocycloalkyl groups such as a cyclobutyl group, a cyclopentyl group, a cyclohexyl group and a cyclooctyl group; polycycloalkyl groups such as an adamantyl group, a norbornyl group, an isobornyl group, a tricyclodecyl group and a tetracyclododecyl group, and the like.

In the alicyclic hydrocarbon group, a part of hydrogen atoms bound to the carbon atom constituting the ring skeleton structure may be substituted by a substituent. Examples of such a substituent include an alkyl group, an alkoxy group, a halogen atom, a halogenated alkyl group, a hydroxyl group, an oxygen atom (=O), and the like.

Although the alkyl group is not particularly limited, an alkyl group having 1 to 5 carbon atoms is preferred, and a methyl group, an ethyl group, an n-propyl group, an i-propyl group, an n-butyl group and a t-butyl group are more preferred.

The alkoxy group and the halogen atom may be each exemplified by examples of the substituent that substitute for a part or all of hydrogen atoms of the aforementioned aliphatic hydrocarbon group.

The alicyclic hydrocarbon group may have a substituent that includes a hetero atom in its ring skeleton structure, and examples of the substituent that includes a hetero atom in such a case include —O—, —C(=O)—O—, —S—, —S(=O)$_2$—, —S(=O)$_2$—O—, and the like.

The aromatic hydrocarbon group is a hydrocarbon group having an aromatic ring. The aromatic hydrocarbon group has carbon atoms of preferably 6 to 30, more preferably 6 to 20, still more preferably 6 to 15, and particularly preferably 6 to 12. However, the number of carbon atoms as referred to herein is shown by excluding the number of carbon atoms in the substituent.

Specific examples of the aromatic hydrocarbon group include aryl groups obtained by eliminating one hydrogen atom from an aromatic hydrocarbon ring such as a phenyl group, a biphenyl group, a fluorenyl group, a naphthyl group, an anthryl group and a phenanthryl group; arylalkyl groups such as a benzyl group, a phenethyl group, a 1-naphthylmethyl group, a 2-naphthylmethyl group, a 1-naphthylethyl group and a 2-naphthylethyl group, and the like. The alkyl chain in the arylalkyl group has carbon atoms of preferably 1 to 4, more preferably 1 to 2, and particularly preferably 1.

The aromatic hydrocarbon group may have one or a plurality of substituents. For example, a part of carbon atoms constituting the aromatic ring included in the aromatic hydrocarbon group may be substituted with a hetero atom, or a hydrogen atom bound to the aromatic ring of the aromatic hydrocarbon group may be substituted by a substituent.

Examples in which a part of carbon atoms constituting the aromatic ring is substituted include: heteroaryl groups in which a part of carbon atoms constituting the ring of the aryl group is substituted with a hetero atom such as an oxygen atom, a sulfur atom or a nitrogen atom; heteroarylalkyl groups in which a part of carbon atoms constituting the aromatic hydrocarbon ring in the arylalkyl group is substituted with the aforementioned hetero atom, and the like.

Examples of the substituent that substitutes for the hydrogen atoms bound to the aromatic ring of the aromatic hydrocarbon group include an alkyl group, an alkoxy group, a halogen atom, a halogenated alkyl group, a hydroxyl group, and the like.

The alkyl group as a substituent of the aromatic hydrocarbon group is preferably an alkyl group having 1 to 5 carbon atoms, and specifically, a methyl group, an ethyl group, a propyl group, an n-butyl group and a t-butyl group are more preferred.

The alkoxy group as a substituent of the aromatic hydrocarbon group is preferably an alkoxy group having 1 to 5 carbon atoms, and specifically, a methoxy group, an ethoxy group, an n-propoxy group, an i-propoxy group, an n-butoxy group and a t-butoxy group are preferred. Of these, a methoxy group and an ethoxy group are more preferred.

Examples of the halogen atom as a substituent of the aromatic hydrocarbon group include a fluorine atom, a chlorine atom, a bromine atom, an iodine atom and the like, and of these, a fluorine atom is preferred. The halogenated alkyl group as a substituent of the aromatic hydrocarbon group is exemplified by a group obtained by substituting a part or all of hydrogen atoms of the aforementioned alkyl group by the halogen atom described above.

In the above formula (2), the bivalent hydrocarbon group represented by $X^{11}$ and $X^{12}$ is exemplified by a group obtained by further eliminating one hydrogen atom from the hydrocarbon group described above to give a bivalent group. The group has carbon atoms of preferably 1 to 30, more preferably 2 to 20, and still more preferably 2 to 10.

Examples of the bivalent hydrocarbon group include bivalent linear or branched chain hydrocarbon groups having 1 to 20 carbon atoms such as a methanediyl group, an ethanediyl group, an n-propane diyl group, an i-propane diyl group, an n-butanediyl group, an n-pentanediyl group, an n-hexanediyl group, an n-heptanediyl group, an n-octanediyl group, an n-nonanediyl group and an n-decanediyl group; bivalent alicyclic hydrocarbon groups having 3 to 20 carbon atoms such as a cyclobutanediyl group, a cyclopentanediyl group, a cyclohexanediyl group, a cyclooctanediyl group, a norbornanediyl group, a tricyclodecanediyl group, a tetracyclododecanediyl group and an adamantane diyl group; arylene groups having 6 to 20 carbon atoms such as a phenylene group and a naphthylene group; arylenealkylene groups having 7 to 20 carbon atoms such as a benzylene group, a phenyleneethylene group, a phenylenepropylene group, a naphthylenemethylene group and a naphthyleneethylene group, and the like.

According to the crosslinking agent, in the above formula (2), it is preferred that $R^{11}$, $R^{12}$ and $R^{13}$ each independently represent a hydrogen atom or an alkyl group having 1 to 8 carbon atoms or an alkenyl group having 2 to 8 carbon atoms; $R^{14}$ and $R^{15}$ each independently represent a hydrogen atom or an alkyl group having 1 to 4 carbon atoms; $X^{11}$ and $X^{12}$ each independently represent an alkanediyl group having 1 to 6 carbon atoms; and m is an integer of 0 to 4. With regard to the alkyl group having 1 to 8 carbon atoms or an alkenyl group having 2 to 8 carbon atoms represented by $R^{11}$, $R^{12}$ and $R^{13}$, the alkyl group having 1 to 4 carbon atoms represented by $R^{14}$ and $R^{15}$, and the alkanediyl group having 1 to 6 carbon atoms represented by $X^{11}$ and $X^{12}$, details in connection with the aliphatic hydrocarbon group and the bivalent hydrocarbon group may be adopted. When the crosslinking agent has such a structure, miscibility with the material to be crosslinked is further improved to permit sufficient progress of the crosslinking, whereby remaining of the crosslinking agent in the crosslinked product can be further diminished, and a crosslinked product further superior in hygienicity and interlayer adhesiveness can be provided.

According to the structure of the crosslinking agent, in the above formula (2), it is more preferred that $R^{11}$, $R^{12}$ and $R^{13}$ represent an alkyl group having 1 to 4 carbon atoms; $R^{14}$ and $R^{15}$ represent a hydrogen atom; $X^{11}$ and $X^{12}$ represent an alkanediyl group having 1 to 3 carbon atoms; and m is 0 or 1. With regard to the alkyl group having 1 to 4 carbon atoms represented by $R^{11}$, $R^{12}$ and $R^{13}$, and the alkanediyl group having 1 to 3 carbon atoms represented by $X^{11}$ and $X^{12}$, details in connection with the aliphatic hydrocarbon group and the bivalent hydrocarbon group may be adopted. When the crosslinking agent has such a specific structure, miscibility with the material to be crosslinked is further enhanced, thereby permitting the crosslinking by the crosslinking agent, of the material to be crosslinked to sufficiently proceed, and bleeding out of the crosslinking agent can be suppressed.

(Physical Properties of Crosslinking Agent (B))

A decomposition temperature of the crosslinking agent (B) is preferably no less than 240° C. In a process for producing a crosslinked product, the crosslinking agent (B) may be brought into a miscible state when the polymer (A) is molded by melt kneading at high temperatures. Also in such a case, when the decomposition temperature of the crosslinking agent (B) is no less than 240° C., decomposition of the crosslinking agent during melt kneading can be prevented, and the level of the crosslinking can be sufficient in the resultant crosslinked product.

The melting point of the crosslinking agent (B) is preferably no greater than 220° C., and more preferably no greater than 210° C. When the melting point of the crosslinking agent (B) falls within such a range, the miscible state of the crosslinking agent in the melting and kneading process as described above can be readily attained.

An SP value of the crosslinking agent (B) is preferably no less than 11.0 $(cal/cm^3)^{1/2}$ and no greater than 14.5 $(cal/cm^3)^{1/2}$, and more preferably no less than 11.5 $(cal/cm^3)^{1/2}$ and no greater than 13.5 $(cal/cm^3)^{1/2}$. When the SP value of the crosslinking agent (B) falls within the above specific range, miscibility with the polyvinyl alcohol type polymer among the polymers (A), particularly EVOH can be enhanced, whereby bleeding out from the crosslinked product can be prevented, and the crosslinked product that is superior in the interlayer adhesiveness and retort resistance can be provided.

(Method for Producing Crosslinking Agent (B))

A method for producing the crosslinking agent (B) represented by the above formula (1) or formula (2) is not particularly limited, and such crosslinking agent (B) may be produced by combining well-known procedures or modifying the same. The crosslinking agent (B) may be produced via a step of allowing an unsaturated carboxylic acid derivative to react with a compound having one or two or more amino groups (hereinafter, merely referred to also as "amino group-containing compound").

The unsaturated carboxylic acid derivative is not particularly limited as long as an amide bond of the crosslinking agent (B), and a structure to be formed thereafter can be provided, and for example, a halide, an ester or an anhydride of an unsaturated carboxylic acid such as acrylic acid, methacrylic acid, crotonic acid, itaconic acid, citraconic acid or sorbic acid, or the like may be exemplified. Of these, a halide of an unsaturated carboxylic acid is preferred in light of enhancement of reactivity with the amino group-containing compound.

The amino group-containing compound is not particularly limited as long as it is a compound having one, or two or more amino groups and provides a structure in which amino groups link to form a main skeleton of the crosslinking agent (B). Examples of such an amino group-containing compound include monoamine compounds such as methylamine, dimethylamine, trimethylamine, ethylamine and propylamine; diamine compounds such as ethylene diamine and trimethylene diamine; triamine compounds such as diethylenetriamine and di(trimethylene)triamine; tetramine compounds such as triethylene tetramine and tri(trimethylene)tetramine, and the like.

The unsaturated carboxylic acid derivative and the amino group-containing compound are both mixed in a solvent in which both are appropriately dissolved together, and the mixture is stirred under a temperature condition of typically no less than –20° C. and no greater than 30° C., and preferably no less than –15° C. and no greater than 0° C. for 1 min to 12 hrs, preferably for 30 min to 8 hrs, whereby a compound can be produced as an intended crosslinking agent.

The amount of the crosslinking agent (B) used in the crosslinkable composition may be determined depending on the degree of crosslinking required for the crosslinked product, and is preferably no less than 0.1 parts by mass and no greater than 30 parts by mass, more preferably no less than 0.5 parts by mass and no greater than 20 parts by mass, and still more preferably no less than 0.8 parts by mass and no greater than 10 parts by mass with respect to 100 parts by mass of the polymer (A). When the amount of the crosslinking agent (B) used falls within the above range, sufficient progress of crosslinking of the polymer (A) is enabled, whereby a crosslinked product that is superior in the retort resistance and interlayer adhesiveness can be obtained.

<Relationship of SP values of Polymer (A) and Crosslinking Agent (B)>

According to the crosslinkable composition, the difference between the SP value of the polymer (A) and the SP value of the crosslinking agent (B) is preferably no greater than 2 $(cal/cm^3)^{1/2}$, more preferably no greater than 1 $(cal/cm^3)^{1/2}$, and particularly preferably no greater than 0.7 $(cal/cm^3)^{1/2}$. Accordingly, a more favorable miscible state between the polymer (A) and the crosslinking agent (B) can be attained.

<Other Components>

The crosslinkable composition may contain other component within a range not to impair the effects of the invention. Examples of the other component include a boron compound, an alkali metal salt, a phosphoric acid compound, an oxidizable substance, other polymer, an oxidization accelerator, other additive, and the like.

(Boron Compound)

Addition of a boron compound to the crosslinkable composition is advantageous in terms of improvement of melt viscosity of EVOH, and the possibility of obtaining a homogenous coextrusion molded product or a coinjection molded material. Examples of the boron compound include boric acids, boric acid ester, boric acid salts, hydrogenated borons, and the like. Specific examples of the boric acids are orthoboric acid (hereinafter, merely referred to also as "boric acid"), metaboric acid, tetraboric acid and the like. Specific examples of the boric acid esters are triethyl borate, trimethyl borate and the like. Specific examples of the boric acid salts are alkali metal salts and alkaline earth metal salts of the aforementioned various types of boric acids, borax, and the like. Of these compounds, orthoboric acid is preferred.

When a boron compound is added, the content in the composition is preferably 20 to 2,000 ppm, and more preferably 50 to 1,000 ppm in terms of boron element equivalent. When the content falls within this range, EVOH accompanied by torque nonuniformity suppressed during heat melting can be obtained. When the content is less than 20 ppm, such an effect is less achievable, whereas when the content exceeds 2,000 ppm, gelation is likely to occur, and the formability may be inferior.

(Alkali Metal Salt)

It is also advantageous for improving the interlayer adhesiveness and the miscibility when an alkali metal salt is added to the crosslinkable composition in an amount of preferably 5 to 5,000 ppm in terms of the alkali metal element equivalent. The amount of the added alkali metal salt is more preferably 20 to 1,000 ppm, and still more preferably 30 to 500 ppm in terms of the alkali metal element equivalent. The alkali metal is exemplified by lithium, sodium, potassium and the like, and the alkali metal salt is exemplified by an aliphatic carboxylic acid salt, an aromatic carboxylic acid salt, a phosphoric acid salt, a metal complex and the like of the alkali metal. Examples of the alkali metal salt include sodium acetate, potassium acetate, sodium phosphate, lithium phosphate, sodium stearate, potassium stearate, a sodium salt of ethylene diamine tetraacetic acid and the like, and of these, sodium acetate, potassium acetate and sodium phosphate are preferable.

(Phosphoric Acid Compound)

The phosphoric acid compound may be added to the crosslinkable composition in an amount of preferably 20 to 500 ppm, more preferably 30 to 300 ppm, and most preferably 50 to 200 ppm in terms of phosphate radical equivalent. When the phosphoric acid compound is blended to fall within the above range, thermal stability of EVOH can be improved. In particular, generation of gel or degraded material and coloring that occur during melt molding carried out for a long period of time can be inhibited.

The type of the phosphoric acid compound added to the crosslinkable composition is not particularly limited, and for example, any of various types of acids such as phosphoric acid and phosphorous acid, and a salt thereof, or the like may be used. The phosphoric acid salt may be any form of a primary phosphoric acid salt, a secondary phosphoric acid salt and a tertiary phosphoric acid salt. Although the cation species is not also particularly limited, an alkali metal or an alkaline earth metal is preferred as the cation species of the phosphoric acid salt. In particular, the phosphorus compound is added preferably in the form of sodium dihydrogen phosphate, potassium dihydrogen phosphate, disodium hydrogen phosphate or dipotassium hydrogen phosphate.

The crosslinkable composition may contain various types of additives within a range not to impair the effects of the invention. Examples of such an additive include an antioxidant, a plasticizer, a heat stabilizer (melt stabilizer), a photoinitiator, a deodorizer, an ultraviolet ray absorber, an antistatic agent, a lubricant, a colorant, a filler, a drying agent, a bulking agent, a pigment, a dye, a processing aid, a fire retardant, an anti-fogging agent, and the like.

<Crosslinking Step of Crosslinkable Composition>

According to the crosslinkable composition, the polymer (A) is crosslinked by the crosslinking agent (B) through imparting an energy from externally. The crosslinking is preferably carried out by heating, or irradiating with at least one activated energy ray selected from the group consisting of an electron beam, an X-ray, a γ-ray, an ultraviolet ray and a visible light ray. Among these, in light of permitting sufficient progress of the crosslinking reaction, it is preferred to carry out crosslinking with the electron beam.

In the case in which an electron beam, an X-ray or a γ-ray is used, the absorbed dose is preferably no less than 1 kGy, more preferably 1 kGy to 1 MGy, still more preferably 5 kGy to 500 kGy, and particularly preferably 10 kGy to 200 kGy. When the absorbed dose is greater than 1 MGy, decomposition of EVOH and the like may occur, and thus the crosslinked product molded into the form of a film may be accompanied by problems of inferior strength, coloring, and the like. Whereas, when the absorbed dose is less than 1 kGy, the degree of crosslinking is not improved, whereby achieving intended performances such as retort resistance may fail.

When irradiation with light is employed, the irradiation time is affected by a thickness of the crosslinked product, a type of the light source, and other various conditions. Irradiation with light may be carried out using a high-pressure mercury vapor lamp, a low-pressure mercury vapor lamp, a carbon arc lamp, a xenon lamp, a metal halide lamp, LED or the like for a time period of at most several minutes, typically within 1 min, and 1 sec or shorter as the case may be.

It is to be noted that the crosslinking step of the crosslinkable composition may be determined to meet the features of the molded product intended, and the step may be carried out either before or after the molding. Particularly, taking into consideration of the adaptability for molding the crosslinkable composition, the crosslinking is preferably carried out after the molding.

<Molding Step of Crosslinkable Composition>

In molding the crosslinkable composition of the present invention, a molding method is appropriately selected such that formation of a variety of molded products, for example, films, sheets, containers, other packing materials, and the like is enabled. In this procedure, the crosslinkable composition may be subjected to molding after forming its pellet once, or the crosslinkable composition prepared by dry blend of each component may be directly subjected to molding.

With regard to the molding method and the molded product, for example, melt extrusion molding can form films, sheets, pipes and the like, injection molding can provide a form of a container, and hollow molding can form hollow containers such as the form of bottles. Hollow molding may include extrusion hollow molding in which extrusion molding is carried out to form a parison, which is then blown, and injection hollow molding in which injection molding is carried out to form a preform, which is then blown. Of these, in order to produce a packing material for retort, a method in which a packing material such as a multilayer film is formed by melt extrusion molding, a method in which a multilayer sheet melt formed by extrusion molding is subjected to heat molding to provide a packing material in the form of a container may be preferably employed. In addition, depending on the use, a method in which extrusion molding is carried out to form a parison, which is subjected to blow molding to provide a comparatively soft packing material in the form of a multilayered container is also preferably used.

<Crosslinked Product and Production Method Thereof>

The crosslinked product of the present invention is obtained from the crosslinkable composition described in the foregoing. Use of the crosslinked product encompasses a broad range. For example, extrusion molded articles, films or sheets (particularly stretched film or thermally shrunk film), heat molded articles, wallpapers or decorative laminate boards, pipes or hoses, profile extrusion articles, extrusion blow molded articles, injection molded articles, flexible packing materials, containers (particularly, retort packing containers) and the like are exemplified as suitable applications. When the molded article is a multilayered structure described later, coextrusion films or coextrusion sheets, thermally shrunk films, multilayer pipes (particularly fuel pipes or pipes for circulating hot water), multilayered hoses (particularly fuel hoses), multilayered containers (particularly coextrusion blow molding containers, coinjection molding containers, retort packing containers) and the like are exemplified as suitable applications.

The method for producing a crosslinked product of the present invention has a step of irradiating the crosslinkable composition with an activated energy ray. Upon irradiation with an activated energy ray, the crosslinkable composition can achieve smooth and sufficient progress of a crosslinking reaction. Among activated energy rays, electron beams are suitable in light of the crosslinking speed and the efficiency of crosslinking. Accordingly, a crosslinked product accompanied by suppressed likelihood of bleeding out, favorable retort resistance and interlayer adhesiveness in combination can be efficiently produced. Details of the method for producing a crosslinked product areas described above in regard to the crosslinking of the crosslinkable composition.

<Multilayered Structure>

The multilayered structure of the present invention is obtained by laminating a layer of a crosslinked product obtained by the molding as described above with other layer.

Provided that: a layer composed of a polymer other than the crosslinkable composition is defined as "x layer"; a crosslinkable composition layer is defined as "y layer"; and an adhesive polymer layer is defined as "z layer", illustrative layer structures of the multilayered structure include, x-y, x-y-x, x-z-y, x-z-y-z-x, x-y-x-y-x, x-z-y-z-x-z-y-z-x, and the like, but not limited thereto. When a plurality of x layers are provided, the types of x layers may be the same or different. Also, a layer formed using a recycled polymer composed of a scrap such as a trim generated during molding may be additionally provided, or alternatively the recycled polymer may be blended in a layer composed of other polymer. Although the construction of each layer of the multilayered structure in terms of the thickness is not particularly limited, in light of the formability and cost, etc., the ratio of a thickness of the y layer with respect to the total layer thickness (total thickness of all layers) is preferably 2 to 20%.

The polymer which may be used in the x layer is preferably a thermoplastic polymer in light of processability and the like. As such a thermoplastic polymer, the following polymers are exemplified, but not particularly limited thereto: polyethylene, polypropylene, ethylene-propylene copolymers, ethylene or propylene copolymers (copolymers of ethylene or propylene with at least one of the following monomers: α-olefins such as 1-butene, isobutene, 4-methyl-1-pentene, 1-hexene and 1-octene; an unsaturated carboxylic acid such as itaconic acid, methacrylic acid, acrylic acid or maleic anhydride, a salt thereof, a partial or complete ester thereof, a nitriles thereof, an amides thereof, and an anhydride of the same; carboxylic acid vinyl esters such as vinyl formate, vinyl acetate, vinyl propionate, vinyl butyrate, vinyl octanoate, vinyl dodecanoate, vinyl stearate or vinyl arachidonate; a vinylsilane type compound such as vinyltrimethoxysilane; an unsaturated sulfonic acid or a salt thereof; an alkylthiol; vinylpyrrolidone, etc.), polyolefins such as poly 4-methyl-1-pentene and poly 1-butene; polyesters such as polyethylene terephthalate, polybutylene terephthalate and polyethylene naphthalate; polyamides such as poly ε-caprolactam, polyhexamethyleneadipamide and polymetaxylyleneadipamide; polyvinylidene chloride, polyvinyl chloride, polystyrene, polyacrylonitriles, polycarbonates, polyacrylates, and the like. Such a thermoplastic polymer layer may be unstretched, or monoaxially or biaxially stretched or rolled. Among these polymers, with regard to those suitably used for retort containers, polyamide, polyester or polypropylene, and particularly polypropylene may be suitably used on an outer layer side of a package in which food or the like is packed. Whereas, polypropylene is suitably used on an inner layer side.

Among these thermoplastic polymers, polyolefins are preferred in light of the moisture resistance, mechanical characteristics, economical efficiency, heat sealing properties and the like, whereas polyesters are preferred in light of mechanical characteristics, heat resistance and the like.

On the other hand, the adhesive polymer used for the z layer is not particularly limited as long as adhesion of each interlayer is allowed, and a polyurethane type or polyester type one-component or two-component curable adhesive, a carboxylic acid-modified polyolefin polymer, or the like may be suitably used. The carboxylic acid-modified polyolefin polymer is an olefin-derived polymer or copolymer that includes an unsaturated carboxylic acid or an anhydride of the same (i.e., maleic anhydride, etc.) as a copolymerization component; or a graft copolymer obtained by subjecting an unsaturated carboxylic acid or an anhydride of the same to grafting with an olefin-derived polymer or copolymer.

Of these, a carboxylic acid-modified polyolefin polymer is more preferred. Particularly, when the x layer is a polyolefin polymer, favorable adhesiveness with the y layer is attained. Examples of the carboxylic acid-modified polyolefin type polymer include polyethylene (low density polyethylene (LDPE), linear low density polyethylene (LLDPE) and very low density polyethylene (VLDPE)), polypropylene, copolymerized polypropylene, an ethylene-vinyl acetate copolymer, an ethylene-(meth)acrylic acid ester (methyl ester or ethyl ester) copolymer and the like which were modified with a carboxylic acid.

As a method for obtaining the multilayered structure, for example, an extrusion lamination method, a dry lamination method, a coinjection molding method, a coextrusion molding method and the like may be exemplified, but not particularly limited thereto. As the coextrusion molding method, a coextrusion lamination method, a coextrusion sheet molding method, a coextrusion inflation molding method, a coextrusion blow molding method and the like may be exemplified.

The sheet, film, parison or the like having a multilayered structure thus obtained is again heated at a temperature of no greater than the melting point of the polymer contained, and then monoaxially or biaxially stretched by a heat molding method such as draw molding, a roll stretching method, a pantograph system stretching method, an inflation stretching method, a blow molding method or the like, whereby a stretched molded product may be obtained.

The multilayered structure is applicable to a variety of usages, and for example, it can be suitably used in application as exemplified in connection with the crosslinked product described above. In particular, in an attempt to take advantages of the multilayered structure such as suppressed likelihood of bleeding out of the crosslinking agent, and favorable retort resistance and interlayer adhesiveness, the multilayered structure can be suitably used in the form of a retort container. Hereinafter, an aspect in which the multilayered structure is utilized as a retort container will be explained.

Use of the multilayered structure enables a flexible retort container to be formed which is constructed with a comparatively thin multilayered structure having a total thickness of all layers (hereinafter, merely referred to also as "total layer thickness") of no greater than 300 μm. In general, such a flexible retort container is processed to have a form of pouch or the like. Since this container is superior in oxygen barrier properties, retort resistance and interlayer adhesiveness, and can be conveniently produced, it is useful in packing a product that is highly sensitive to oxygen and is likely to deteriorate.

The thickness of such a multilayered structure (multilayer film) is typically no greater than 300 μm, more preferably no greater than 250 μm, and still more preferably no greater than 200 μm as described above in light of maintaining the transparency and flexibility. On the other hand, taking into consideration mechanical characteristics as a container, the total layer thickness is preferably no less than 10 μm, more preferably no less than 20 μm, and still more preferably no less than 30 μm.

When a retort container constructed with a multilayer film having the total layer thickness of no greater than 300 μm is produced from a multilayer film, a method for producing the multilayer film is not particularly limited, and for example, the multilayer film can be obtained by lamination according to a method such as dry lamination or coextrusion lamination of a layer constituted with the crosslinkable composition and a thermoplastic resin layer.

When dry lamination is employed, an unstretched film, a monoaxially stretched film, a biaxially stretched film, a rolled film or the like may be used. Of these, a biaxially stretched polypropylene film, a biaxially stretched polyethylene terephthalate film, a biaxially stretched poly ϵ-caprolactam film is preferred in light of the mechanical strength, and a biaxially stretched polypropylene film is particularly preferable taking into consideration also the moisture-proof property. When an unstretched film or a monoaxially stretched film is used, the stretched multilayer film can be obtained by heating again the multilayer film after lamination, and monoaxially or biaxially stretched by a heat molding method such as draw molding, a roll stretching method, a pantograph system stretching method, an inflation stretching method or the like.

For sealing the obtained multilayered container, it is also preferred that a layer constituted with a heat sealable resin is provided on the surface of at least one outermost layer in the step of producing the multilayer film. Such a resin may be exemplified by a polyolefin such as polyethylene or polypropylene.

The multilayer film thus obtained is processed into, for example, a form of a pouch, whereby a retort container for packing the content can be provided. Due to being flexible and convenient, and being superior in transparency and oxygen barrier properties, the retort container is useful for packing a content that is likely to deteriorate in the presence of oxygen, particularly food, as well as pet food, medical drug, or the like.

<Crosslinking Agent>

The crosslinking agent of the present invention is represented by the above formula (2). A material to be crosslinked by the crosslinking agent is not particularly limited, provided that it is miscible with the crosslinking agent and can be reacted therewith, and is preferably a polymer having an SP value of no less than 9.5 $(cal/cm^3)^{1/2}$ and no greater than 16.5 $(cal/cm^3)^{1/2}$. Examples of the polymer include a polyvinyl alcohol type polymer, polyamide, polyacrylonitrile, and the like described above. Among these, a polyvinyl alcohol type polymer, and particularly EVOH is preferred. The crosslinked product may be similar to those exemplified as the compound represented by the formula (2) in the crosslinking agent (B) of the crosslinkable composition described above.

<Compound>

The compound of the present invention is represented by the above formula (2').

In the formula (2'), $R^{11}$, $R^{12}$ and $R^{13}$ each independently represent an alkyl group having 1 to 8 carbon atoms or an alkenyl group having 2 to 8 carbon atoms; $R^{14}$ and $R^{15}$ each independently represent a hydrogen atom or an alkyl group having 1 to 4 carbon atoms; $X^{11}$ and $X^{12}$ each independently represent an alkanediyl group having 1 to 6 carbon atoms; m is an integer of 0 to 4, and provided that m is an integer of at least 2, a plurality of $R^{12}$s each independently represent an alkyl group having 1 to 8 carbon atoms or an alkenyl group having 2 to 8 carbon atoms, and a plurality of $X^{12}$s each independently represent an alkanediyl group having 1 to 6 carbon atoms. Specific examples of the group represented by $R^{11}$ to $R^{15}$, and $X^{11}$ and $X^{12}$ are involved in those exemplified in connection with the compound represented by the formula (2) in the crosslinking agent (B).

Since the compound has a specific structure represented by the above formula (2'), it can be suitably used as a crosslinking agent, etc., of a material to be crosslinked such as, for example, a polymer having an SP value of no less than 9.5 $(cal/cm^3)^{1/2}$ and no greater than 16.5 $(cal/cm^3)^{1/2}$, particularly a polyvinyl alcohol type polymer.

<Method for Producing the Compound>

The method for producing a compound of the present invention includes a step of allowing an unsaturated carboxylic acid derivative to react with a compound having at least two amino groups. Details of the production method are involved in those described above in connection with the method for producing the crosslinking agent (B). According to the production method, the compound can be efficiently produced.

EXAMPLES

Hereinafter, modes for carrying out the present invention are explained in more detail by way of Examples. However, the present invention is not in any way limited to these Examples. Herein, "part" is on mass basis unless otherwise stated in particular. Each measurement and evaluation in Examples and Comparative Examples was performed according to the following particulars.

(1) Gel Fraction

In 100 parts by mass of a mixed solvent of water (15% by mass) and phenol (85% by mass) was immersed 1 part by mass of a monolayer film, and the solvent was heated at 60° C. for 12 hrs to permit dissolution, followed by filtration. The filtrate was evaporated to dryness, and the solid matter residue (%) was calculated, which was defined as a gel fraction.

(2) Retort Resistance (Monolayer)

A pellet of a crosslinkable composition obtained in the following Examples and Comparative Examples was subjected to melt extrusion in a 20 mmϕ monoaxial extruder at 210° C. with a coat hanger die to obtain a monolayer film having a thickness of 20 μm. This monolayer film was introduced into an electron beam irradiator (Curetron: manufactured by NHV Corporation), and crosslinking was permitted by irradiating with an electron beam at an accelerating voltage of 250 kV to obtain an irradiated monolayer film. After the irradiated monolayer film thus obtained was subjected to a retorting process at 120° C. for 30 min, the appearance of the film was observed by visual inspection. The appearance of the film was evaluated according to the following criteria:

A: dissolution of the film not found entirely;
B: dissolution of the film found in part; and
C: dissolution of the film found entirely, with the original film shape lost.

(3) Retort Resistance (Multilayer)

A stretched nylon film (ON) and unstretched polypropylene film (CPP) were laminated on both sides of a monolayer constituted with a crosslinkable resin composition obtained similarly to the paragraph (2) described above via an adhesive for anchor coating (Ac) to obtain a multilayer film ((outer layer) ON 15 μm/Ac/EVOH layer (monolayer film) 20 μm/Ac/CPP 50 μm (inner layer)). The multilayer film thus obtained was introduced into an electron beam irradiator (Curetron: manufactured by NHV Corporation), and crosslinking was permitted by irradiating with an electron beam at an accelerating voltage of 250 kV to obtain an irradiated multilayer film. A pouch using the irradiated multilayer film thus obtained was produced, and water was poured thereinto. After carrying out a retorting process at 120° C. for 30 min, the appearance of the pouch was observed by visual inspection. The appearance of the pouch was evaluated according to the following criteria:

A: delamination of the EVOH layer, and the inner and outer layers not confirmed, with the transparency of the EVOH layer maintained; and
B: delamination of a part of the EVOH layer, and the inner and outer layers, or blooming of the EVOH layer found.

(4) OTR (Oxygen Transmission Rate; Prior to Retort)

OTR was measured using an irradiated multilayer film obtained similarly to the paragraph (3) described above.

Conditions: 20° C.; and (external) 65% RH/(internal) 100% RH (5) OTR (Oxygen Transmission Rate; after Retorting)

A pouch was produced using an irradiated multilayer film obtained similarly to the paragraph (3) described above, and water was poured thereinto. After carrying out a retorting process at 120° C. for 30 min, OTR was measured.

Conditions: 20° C., (external) 65% RH/(internal) 100% RH, 1 day after the retorting (6) Adhesiveness (Evaluation as Marker of Bleeding Out)

After the irradiated monolayer film obtained similarly to the paragraph (2) described above was stored under conditions including a temperature of 30° C. and an RH of 80% for three months, it was laminated with a CPP film (50 μm) using an adhesive for anchor coating. After the laminate was subjected to an aging treatment at 40° C., for 2 days, the adhesiveness was evaluated:

A: adhesiveness being favorable, without occurrence of delamination even if a force is applied thereto;

B: being favorably adhered, but may be accompanied by delamination upon application of a force; and C: delamination not found in general use, but may be accompanied by delamination upon application of a force.

In the following Examples 1 to 7 and Comparative Examples 1 to 5, EVOH and crosslinking agents having the following compositions and physical properties were used as ethylene-vinyl alcohol copolymers:

(EVOH-1)
ethylene content: 27 mol %
degree of saponification: 99.8%
SP value: 12.60 $(cal/cm^3)^{1/2}$ (EVOH-2)
ethylene content: 32 mol %
degree of saponification: 99.8%
SP value: 12.31 $(cal/cm^3)^{1/2}$ (Crosslinking Agent 1)

Diethylenetriscrotoamide represented by the following formula was used as crosslinking agent 1.

[chemical formula 4]

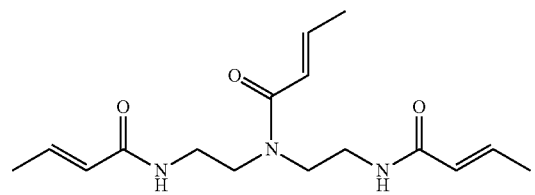

Diethylene triscrotoamide was synthesized according to the following procedure. Into a 1 L separable flask were charged 46.42 g of diethylenetriamine (0.45 mol), 270 g of water, 223.9 g of potassium carbonate (1.62 mol) and 135 mL of tetrahydrofuran. The internal temperature was lowered to about −10° C. using a cooling bath, and thereto was slowly added 150.53 g of crotonoyl chloride (1.44 mol) dropwise while stirring the mixture. In this step, the rate of addition of crotonoyl chloride dropwise was regulated such that the internal temperature became no greater than −5° C. After completing the dropwise addition, the bath was changed to an ice water bath, and the mixture was stirred for 1 hour. Then, the bath was changed to a water bath, followed by additional stirring for 1 hour. Thereto was added 600 mL of water, and extracted with about 400 mL of a mixture of 1:1 of xylene and 1-propanol. Thereafter, 200 mL of an aqueous solution containing 20% by mass sodium chloride and 5% by mass phosphoric acid was added to the oil layer, and liquid separation was carried out. Subsequently, 20% by mass sodium chloride and 5% by mass sodium carbonate were added to the oil layer, and liquid separation was carried out. Anhydrous magnesium sulfate (about 5% by mass) was added to the oil layer, and the mixture was filtered, followed by concentration by an evaporator. The resultant solid matter was recrystallized with butyl acetate to give 120 g of diethylene triscrotoamide (SP value: 12.04 $(cal/cm^3)^{1/2}$, melting point: 144° C., decomposition temperature: 300° C.). Identification of the sample obtained was carried out by $^1$H-NMR determination (using "model JNM-GX-500" manufactured by JEOL, Ltd.,) in deuterated dimethyl sulfoxide as a solvent. 1.6 to 1.8 ppm (9H): methyl site, 3.1 to 3.5 ppm (8H): methylene site, 5.8 to 6.8 ppm (6H): methylene site of double bond, 7.7 ppm (2H): amine moiety.

(Crosslinking Agent 2)

Ethylenebiscrotoamide represented by the following formula was used as crosslinking agent 2.

[chemical formula 5]

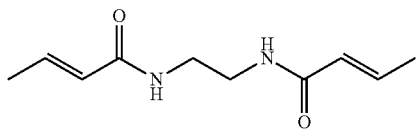

Ethylenebiscrotoamide was synthesized according to the following procedure. Into a 1 L separable flask were charged 40.66 g of ethylene diamine (0.7 mol), 420 g of water and 212.84 g of potassium carbonate (1.54 mol). The internal temperature was lowered to about −10° C. using a cooling bath, and thereto was slowly added 156.67 g of crotonoyl chloride (1.47 mol) dropwise while stirring the mixture. In this step, the rate of addition of crotonoyl chloride dropwise was regulated such that the internal temperature became no greater than −5° C. After completing the dropwise addition, the bath was changed to an ice water bath, and the mixture was stirred for 1 hour. Then, the bath was changed to a water bath, followed by additional stirring for 1 hour. Thereto was added 400 mL of water, and the mixture was filtered. The solid matter and 1350 g of water were transferred into a 2 L separable flask, and dissolution was permitted by boiling, followed by filtration and cooling to obtain a solid matter. The solid matter was dried under reduced pressure to give 65 g of ethylenebiscrotoamide (SP value: 11.98 $(cal/cm^3)^{1/2}$, melting point: 210° C., decomposition temperature: 250° C.). Identification of the sample obtained was carried out by $^1$H-NMR determination (using "model JNM-GX-500" manufactured by JEOL, Ltd.,) in deuterated dimethyl sulfoxide as a solvent. 1.6 to 1.8 ppm (6H): methyl site, 3.1 to 3.5 ppm (4H): methylene site, 5.8 to 6.8 ppm (4H): methylene site of double bond, 8.0 ppm (2H): amine moiety.

(Crosslinking Agent 3)

Triallyl cyanurate (TAC, SP value: 11.32 $(cal/cm^3)^{1/2}$)

[chemical formula 6]

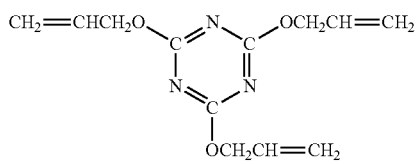

(Crosslinking Agent 4)
Diallyl maleate (DAM, SP value: 9.78 (cal/cm³)^(1/2))

[chemical formula 7]

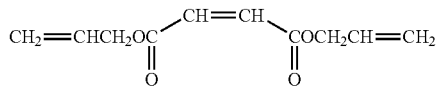

(Crosslinking Agent 5)
Pentaerythritol triallyl ether (PETAE, SP value: 9.81 (cal/cm³)^(1/2))

[chemical formula 8]

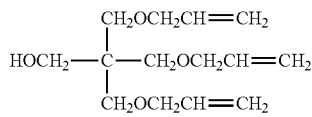

Examples 1 to 7 and Comparative Examples 1 to 5

Using a 25 mmφ biaxial extruder, a pellet of a crosslinkable resin composition was prepared by melt kneading the aforementioned EVOH and crosslinking agent at proportions which in Table 1 at 210° C. The irradiation dose in each evaluation was as shown in Table 1. The results of the evaluations are shown in Table 1.

film obtained using the composition of Comparative Examples exhibited results inferior in either the retort resistance and OTR after the retorting, or the adhesiveness.

INDUSTRIAL APPLICABILITY

The crosslinkable composition of the present invention enables bleeding out of a crosslinking agent from a crosslinked product to be sufficiently suppressed, and can provide a hygienic crosslinked product that is superior in retort resistance and interlayer adhesiveness. Therefore, the crosslinkable composition of the present invention can be suitably used for producing food packaging materials and other packaging materials.

The invention claimed is:
1. A crosslinkable composition comprising:
   (A) a polymer having an SP value of no less than 9.5 (cal/cm³)^(1/2) and no greater than 16.5 (cal/cm³)^(1/2); and
   (B) a crosslinking agent having one or more polar groups and two or more polymerizable groups, wherein the polar groups comprise an oxygen atom and a nitrogen atom that are not part of an aromatic ring.
2. The crosslinkable composition of claim 1, wherein a decomposition temperature of the crosslinking agent (B) is no less than 240° C.
3. The crosslinkable composition of claim 1, wherein a difference between the SP value of the polymer (A) and an SP value of the crosslinking agent (B) is no greater than 2 (cal/cm³)^(1/2).

TABLE 1

| | Crosslinkable composition | | | Difference between SP values*² | Electron beam irradiation dose (kGy) | Gel fraction (%) | Retort resistance | | OTR*³ | | Adhesiveness |
|---|---|---|---|---|---|---|---|---|---|---|---|
| | EVOH | Crosslinking agent | Amount added*¹ | | | | Mono-layer | Multi-layer | Before retorting | After retorting | |
| Example 1 | EVOH-1 | crosslinking agent 1 | 1 | 0.56 | 100 | 29 | A | A | 0.3 | 1.2 | A |
| Example 2 | EVOH-1 | crosslinking agent 1 | 2 | 0.56 | 100 | 40 | A | A | 0.3 | 0.9 | A |
| Example 3 | EVOH-1 | crosslinking agent 1 | 4 | 0.56 | 100 | 51 | A | A | 0.1 | 0.7 | A |
| Example 4 | EVOH-2 | crosslinking agent 1 | 4 | 0.27 | 100 | 49 | A | A | 0.2 | 1.3 | A |
| Example 5 | EVOH-1 | crosslinking agent 1 | 4 | 0.56 | 30 | 31 | A | A | 0.3 | 1.1 | A |
| Example 6 | EVOH-1 | crosslinking agent 1 | 4 | 0.56 | 10 | 23 | A | A | 0.4 | 1.3 | A |
| Example 7 | EVOH-1 | crosslinking agent 2 | 4 | 0.62 | 100 | 32 | A | A | 0.3 | 1.1 | A |
| Comparative Example 1 | EVOH-1 | — | — | — | — | 0 | C | B | 0.4 | 2.7 | A |
| Comparative Example 2 | EVOH-1 | — | — | — | 100 | 0 | C | B | 0.4 | 2.7 | A |
| Comparative Example 3 | EVOH-1 | crosslinking agent 3 | 4 | 1.28 | 100 | 50 | A | A | 0.2 | 2.3 | C |
| Comparative Example 4 | EVOH-1 | crosslinking agent 4 | 4 | 2.82 | 100 | 45 | A | A | 0.2 | 2.4 | C |
| Comparative Example 5 | EVOH-1 | crosslinking agent 5 | 4 | 2.79 | 100 | 35 | A | A | 0.2 | 2.1 | C |

*¹Amount of crosslinking agent with respect to 100 parts by mass of EVOH (parts by mass)
*²Unit: (cal/cm³)^(1/2)
*³Unit: cc/m² · day · atm As is clear also from the results shown in Table 1, in each film obtained using the crosslinkable composition according to Examples, the gel fraction was high, indicating sufficient progress of the crosslinking. Therefore, the results from each film of Examples indicated superior retort resistance and low OTR, as well as favorable adhesiveness. To the contrary, the 4. The crosslinkable composition of claim 3, wherein the difference between the SP value of the polymer (A) and the SP value of the crosslinking agent (B) is no greater than 1 (cal/cm³)^(1/2).
5. The crosslinkable composition of claim 1, wherein a melting point of the crosslinking agent (B) is no greater than 220° C.

6. The crosslinkable composition of claim 1, wherein the polar group of the crosslinking agent (B) is an amide group, and the polymerizable groups are each independently an unsaturated hydrocarbon group having 2 to 12 carbon atoms.

7. The crosslinkable composition of claim 6, wherein the crosslinking agent (B) comprises 2 or 3 amide groups, and 2 or 3 unsaturated hydrocarbon groups having 2 to 12 carbon atoms.

8. The crosslinkable composition of claim 6, wherein the unsaturated hydrocarbon group is a vinyl group, or an alkenyl group or an alkadienyl group having 3 to 12 carbon atoms.

9. The crosslinkable composition of claim 1, wherein the crosslinking agent (B) is represented by formula (1):

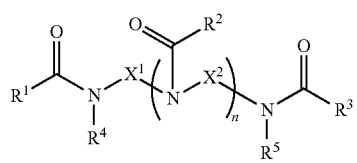

wherein $R^1$, $R^2$ and $R^3$ each independently represent an unsaturated hydrocarbon group having 2 to 8 carbon atoms; $R^4$ and $R^5$ each independently represent a hydrogen atom or an alkyl group having 1 to 4 carbon atoms; $X^1$ and $X^2$ each independently represent an alkanediyl group having 1 to 6 carbon atoms; and n is an integer of 0 to 4, wherein a plurality of $R^2$s each independently represent an unsaturated hydrocarbon group having 2 to 8 carbon atoms and a plurality of $X^2$s each independently represent an alkanediyl group having 1 to 6 carbon atoms.

10. The crosslinkable composition of claim 9, wherein $R^1$, $R^2$ and $R^3$ each independently represent a vinyl group or an alkenyl group having 3 to 6 carbon atoms; $R^4$ and $R^5$ represent a hydrogen atom; $X^1$ and $X^2$ each independently represent an alkanediyl group having 1 to 3 carbon atoms; and n is 0 or 1.

11. The crosslinkable composition of claim 9, wherein the polymer (A) is a polyvinyl alcohol type polymer.

12. The crosslinkable composition of claim 1, wherein the polyvinyl alcohol type polymer is an ethylene-vinyl alcohol copolymer.

13. The crosslinkable composition of claim 1, wherein the polymer (A) is a polyvinyl alcohol type polymer.

14. The crosslinkable composition of claim 13, wherein the polyvinyl alcohol type polymer is an ethylene-vinyl alcohol copolymer.

15. The crosslinkable composition of claim 1, which is crosslinkable by an activated energy ray.

16. The crosslinkable composition of claim 15, wherein the activated energy ray is an electron beam.

17. A crosslinked product comprising, in reacted form, the crosslinkable composition of claim 1.

18. The crosslinked product of claim 17, which is in the form of a film.

19. A multilayered structure comprising layers comprising the crosslinked product of claim 17.

20. The multilayered structure of claim 19, which is a retort container.

21. A method for producing a crosslinked product, the method comprising irradiating the crosslinkable composition of claim 15 with an activated energy ray.

22. The method of claim 21, wherein the activated energy ray is an electron beam.

23. A crosslinking agent represented by formula (2):

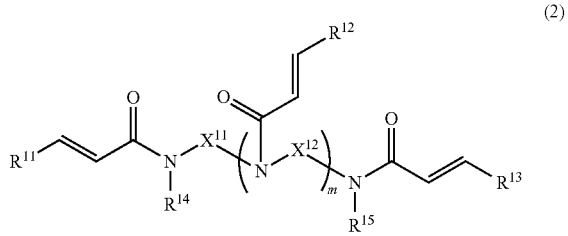

wherein $R^{11}$, $R^{12}$, $R^{13}$, $R^{14}$ and $R^{15}$ each independently represent a hydrogen atom or a hydrocarbon group which optionally has a substituent; $X^{11}$ and $X^{12}$ each independently represent a bivalent hydrocarbon group; m is an integer of 0 to 4, wherein a plurality of $R^{12}$s each independently represent a hydrogen atom or a hydrocarbon group which optionally has a substituent, and a plurality of $X^{12}$s each independently represent a bivalent hydrocarbon group.

24. The crosslinking agent of claim 23, wherein $R^{11}$, $R^{12}$ and $R^{13}$ each independently represent a hydrogen atom or an alkyl group having 1 to 8 carbon atoms or an alkenyl group having 2 to 8 carbon atoms; $R^{14}$ and $R^{15}$ each independently represent a hydrogen atom or an alkyl group having 1 to 4 carbon atoms; $X^{11}$ and $X^{12}$ each independently represent an alkanediyl group having 1 to 6 carbon atoms; and m is an integer of 0 to 4.

25. The crosslinking agent of claim 23, wherein $R^{11}$, $R^{12}$ and $R^{13}$ represent an alkyl group having 1 to 4 carbon atoms; $R^{14}$ and $R^{15}$ represent a hydrogen atom; $X^{11}$ and $X^{12}$ each independently represent an alkanediyl group having 1 to 3 carbon atoms; and m is 0 or 1.

26. The crosslinking agent of claim 23, which has a decomposition temperature of no less than 240° C.

27. The crosslinking agent claim 23, which has a melting point of no greater than 220° C.

28. The crosslinking agent of claim 23, which has an SP value of no less than 11.0 (cal/cm$^3$)$^{1/2}$ and no greater than 14.5 (cal/cm$^3$)$^{1/2}$.

29. A composition comprising a polyvinyl alcohol type polymer crosslinked by the crosslinking agent of claim 23.

30. The composition of claim 29, wherein the polyvinyl alcohol type polymer is an ethylene-vinyl alcohol copolymer.

31. A compound represented by formula (2'):

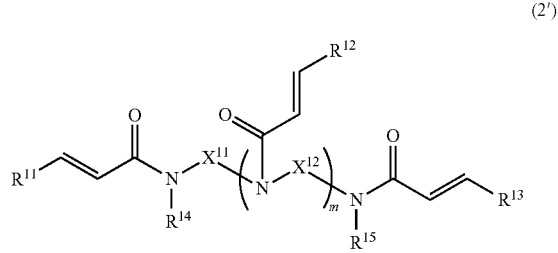

wherein $R^{11}$, $R^{12}$ and $R^{13}$ each independently represent an alkyl group having 1 to 8 carbon atoms or an alkenyl group having 2 to 8 carbon atoms; $R^{14}$ and $R^{15}$ each independently represent a hydrogen atom or an alkyl group having 1 to 4 carbon atoms; $X^{11}$ and $X^{12}$ each independently represent an alkanediyl group having 1 to 6 carbon atoms; m is an integer of 0 to 4, wherein a plurality of $R^{12}$s each independently represent an alkyl group having 1 to 8 carbon atoms or an alkenyl group having 2 to 8 carbon atoms, and a plurality of $X^{12}$s each independently represent an alkanediyl group having 1 to 6 carbon atoms.

32. A method for producing the compound of claim 31, the method comprising reacting an unsaturated carboxylic acid derivative with a compound having at least two amino groups.

* * * * *

UNITED STATES PATENT AND TRADEMARK OFFICE
CERTIFICATE OF CORRECTION

Page 1 of 1

| | |
|---|---|
| PATENT NO. | : 8,617,678 B2 |
| APPLICATION NO. | : 13/634105 |
| DATED | : December 31, 2013 |
| INVENTOR(S) | : Kaoru Ikeda et al. |

It is certified that error appears in the above-identified patent and that said Letters Patent is hereby corrected as shown below:

In the Claims:

In column 29, line 43 please amend claim 12 as follows:

12. The crosslinkable composition of claim [[1]] 11, wherein the polyvinyl alcohol type polymer is an ethylene-vinyl alcohol copolymer.

Signed and Sealed this
Twenty-third Day of September, 2014

Michelle K. Lee
*Deputy Director of the United States Patent and Trademark Office*